(12) United States Patent
Deal

(10) Patent No.: US 9,211,395 B2
(45) Date of Patent: Dec. 15, 2015

(54) EXPANDABLE SHEATH

(75) Inventors: Travis Deal, Freedom, IN (US); Nancy Deal, legal representative, Freedom, IN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 225 days.

(21) Appl. No.: 13/323,450

(22) Filed: Dec. 12, 2011

(65) Prior Publication Data

US 2012/0158033 A1 Jun. 21, 2012

Related U.S. Application Data

(60) Provisional application No. 61/425,131, filed on Dec. 20, 2010.

(51) Int. Cl.
*A61M 29/00* (2006.01)
*A61M 25/00* (2006.01)

(52) U.S. Cl.
CPC ....... *A61M 29/00* (2013.01); *A61M 2025/0024* (2013.01)

(58) Field of Classification Search
CPC ..................................................... A61M 29/00
USPC ......................................................... 606/193
See application file for complete search history.

(56) References Cited

U.S. PATENT DOCUMENTS

| | | | | |
|---|---|---|---|---|
| 4,984,564 A | * | 1/1991 | Yuen | 600/207 |
| 5,795,289 A | * | 8/1998 | Wyttenbach | 600/207 |
| 5,824,054 A | * | 10/1998 | Khosravi et al. | 623/1.44 |
| 8,403,913 B2 | * | 3/2013 | Dein | 604/541 |
| 2003/0236445 A1 | * | 12/2003 | Couvillon, Jr. | 600/114 |
| 2005/0124937 A1 | * | 6/2005 | Kick et al. | 604/164.1 |
| 2005/0209627 A1 | * | 9/2005 | Kick et al. | 606/191 |
| 2007/0244550 A1 | * | 10/2007 | Eidenschink | 623/1.49 |
| 2008/0221552 A1 | * | 9/2008 | Leonard | 604/509 |
| 2009/0209969 A1 | * | 8/2009 | Wolfe | 606/108 |
| 2009/0227962 A1 | * | 9/2009 | Eversull et al. | 604/265 |
| 2012/0101480 A1 | * | 4/2012 | Ingle et al. | 604/526 |

OTHER PUBLICATIONS

Definition of "adjacent", Dictionary.com, accessed on Sep. 13, 2013.*

* cited by examiner

*Primary Examiner* — Tuan V Nguyen
(74) *Attorney, Agent, or Firm* — Bookoff McAndrews, PLLC

(57) ABSTRACT

A medical device includes an elongate member and an expandable member. The elongate member has an inner surface and an outer surface. The inner surface defines a lumen. The elongate member has a collapsed configuration and an expanded configuration and is biased to its collapsed configuration. The expandable member is coupled to the outer surface of the elongate member. The expandable member is configured to move the elongate member from its collapsed configuration to its expanded configuration.

16 Claims, 4 Drawing Sheets

EXPANDABLE SHEATH

CROSS-REFERENCE TO RELATED APPLICATION

This application is a Nonprovisional of, and claims priority to, U.S. Patent Application No. 61/425,131, filed Dec. 20, 2010, entitled "EXPANDABLE SHEATH", which is incorporated by reference herein in its entirety.

TECHNICAL FIELD

This disclosure relates generally sheaths for use during medical procedures and more particularly to expandable sheaths.

BACKGROUND

A variety of medical procedures make use of sheaths such as expandable sheaths. For example, in some medical procedures a sheath is placed into the body of a patient to dilate bodily tissue, define and/or create an opening through which additional medical devices may be placed or inserted. Some of the known sheaths are expandable such that the sheath may be placed or inserted within the body of the patient in a first or collapsed configuration. Then once placed within the body of the patient, the sheath may be moved to a second or expanded configuration. Such sheaths also typically define a lumen. Thus, in the expanded configuration, such known sheaths define or create a workable opening or lumen within the body of the patient through which additional medical steps may be performed.

During the placement of such sheaths, however, the sheaths might extend proximate to strictures or narrow portions of the body of the patient. In such instances, some known sheaths may be difficult to maneuver or remove from the body of the patient after the sheath has been expanded. Specifically, some known sheaths may expand such that the expanded sheath expands around a stricture to surround the stricture (often described as "hour-glassing"). As known expandable sheaths are not configured to return to their collapsed configurations, it may be difficult, painful, and/or potentially damaging to the body of the patient to move the expanded portion of the sheath past the stricture.

Accordingly, it is desirable to provide a sheath that is configured to return to its collapsed configuration such that it would be able to more easily move past a stricture or narrow portion of the body of the patient.

SUMMARY

A medical device includes an elongate member and an expandable member. The elongate member has an inner surface and an outer surface. The inner surface defines a lumen. The elongate member has a collapsed configuration and an expanded configuration and is biased to its collapsed configuration. The expandable member is coupled to the outer surface of the elongate member. The expandable member is configured to move the elongate member from its collapsed configuration to its expanded configuration.

DETAILED DESCRIPTION

The devices and methods described herein are generally directed to medical devices. In some embodiments, the medical devices can be inserted into a body of a patient and used to create or provide an opening for further medical procedures. For example, in some embodiments, the medical devices are access sheaths or dilators, which once inserted into a body of a patient, dilate bodily tissue to provide a working channel or lumen into which additional medical devices may be inserted. In some embodiments, the access sheaths may be inserted into a body of a patient such that they extend from a location outside of a body of a patient to a location proximate a urinary tract of a patient. Specifically, in some embodiments, the access sheaths may be inserted into a body of a patient such that the sheath extends from a position or location outside of the body of the patient to a location within a kidney of the patient. In other embodiments, the medical devices disclosed herein are configured to be inserted and extend through other portions of the body of the patient.

As used herein, the terms proximal portion or proximal end refer to the portion or end, respectively, of a device that is closest to a physician when performing a medical procedure, and the terms distal portion or distal end refer to the portion or end, respectively, of the device that is furthest from the physician during a medical procedure. For example, a distal end or portion of an insertion tool or device as described herein refers to the end or portion of the device that is first inserted into a body of a patient during a medical procedure. The proximal end or portion is the end or portion of the device that is remains outside of the body of the patient during the insertion procedure (or if the entire device is inserted into the body of the patient during the delivery procedure, the proximal end portion is inserted into a body of the patient after the distal end or distal portion is inserted).

Figure 1:
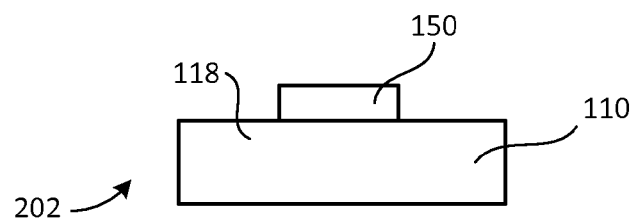
FIG. 1 is a schematic illustration of a medical device according to an embodiment.

FIG. 1 is a schematic illustration of a medical device 100 according to an embodiment of the invention. The medical device 100 includes an elongate member 110 and an expandable member 150. The expandable member 150 is coupled to an outer surface 118 of the elongate member 110. In some embodiments, the expandable member 150 defines a lumen (not illustrated) and the expandable member 150 is coupled to the elongate member 110 such that the elongate member 110 is disposed within the lumen defined by the expandable member 150.

The elongate member 110 defines a lumen (not illustrated) and is configured to be disposed or placed in a first configuration and a second configuration. In some embodiments, the first configuration is a collapsed configuration and the second configuration is an expanded configuration. In some embodiments, the lumen defined by the elongate member 110 has a first size when the elongate member 110 is in its collapsed configuration and has a second size when the elongate member 110 is in its expanded configuration. For example, in some embodiments, the diameter of the lumen defined by the elongate member 110 is larger when the elongate member 110 is in its expanded configuration than when the elongate member 110 is in its collapsed configuration.

In some embodiments, the elongate member 110 is biased to its collapsed configuration. In other embodiments, the elongate member 110 is biased to its expanded configuration. In yet other embodiments, the elongate member 110 is not biased to either of its collapsed or expanded configurations.

In some embodiments, the lumen defined by the elongate member 110 is configured to receive another medical device so that such other medical device extends through the lumen defined by the elongate member 110. For example, in some embodiments, when the elongate member 110 is placed within a body of a patient and is in its expanded configuration, another medical device, such as a guidewire or stent, may be inserted into the body of the patient through the lumen defined by the elongate member 110.

In some embodiments, the elongate member 110 is generally tubular and defines a lumen that has a generally circular cross-section. For example, in some embodiments, the elongate member 110 is a spiral roll. In other embodiments, the elongate member 110 has a different shape and defines a lumen with a non-circular cross-section.

The expandable member 150 is configured to move or convert the elongate member 110 from one configuration to another configuration. For example, in some embodiments, the expandable member 150 is configured to expand the elongate member or move the elongate member from its first, collapsed configuration to its second, expanded configuration.

In some embodiments, the expandable member 150 is configured to be expanded from a first, collapsed configuration to a second, expanded configuration. For example, in some embodiments, the expandable member 150 is an inflatable member. In such embodiments, when the inflatable member is moved or expanded from a deflated configuration to an inflated configuration, the elongate member 110 is moved from its collapsed configuration to its expanded configuration. Additionally, in such embodiments, the inflatable member may include a valve and an inflation lumen to facilitate the inflation of the inflatable member. In other embodiments, another mechanism is may be used to inflate the inflatable member.

In other embodiments, the expandable member 150 includes other mechanisms for expanding the elongate member from a first configuration to a second configuration.

The expandable member 150 may be coupled to the elongate member 110 using any known method. For example, in some embodiments, an adhesive couples the expandable member 150 to the elongate member 110. In another embodiment, the expandable member 150 is heat welded to the elongate member 110. In yet further embodiments glue or an ultrasonic welding process is used to couple the expandable member 150 to the elongate member 110.

The expandable member 150 and the elongate member 110 may be made of any biocompatible material. For example, in some embodiments, the expandable member 150 and the elongate member 110 are made of a biocompatible plastic material. In other embodiments, the expandable member 150 and/or the elongate member 110 are made of or include a super elastic Nitinol.

Figure 2:
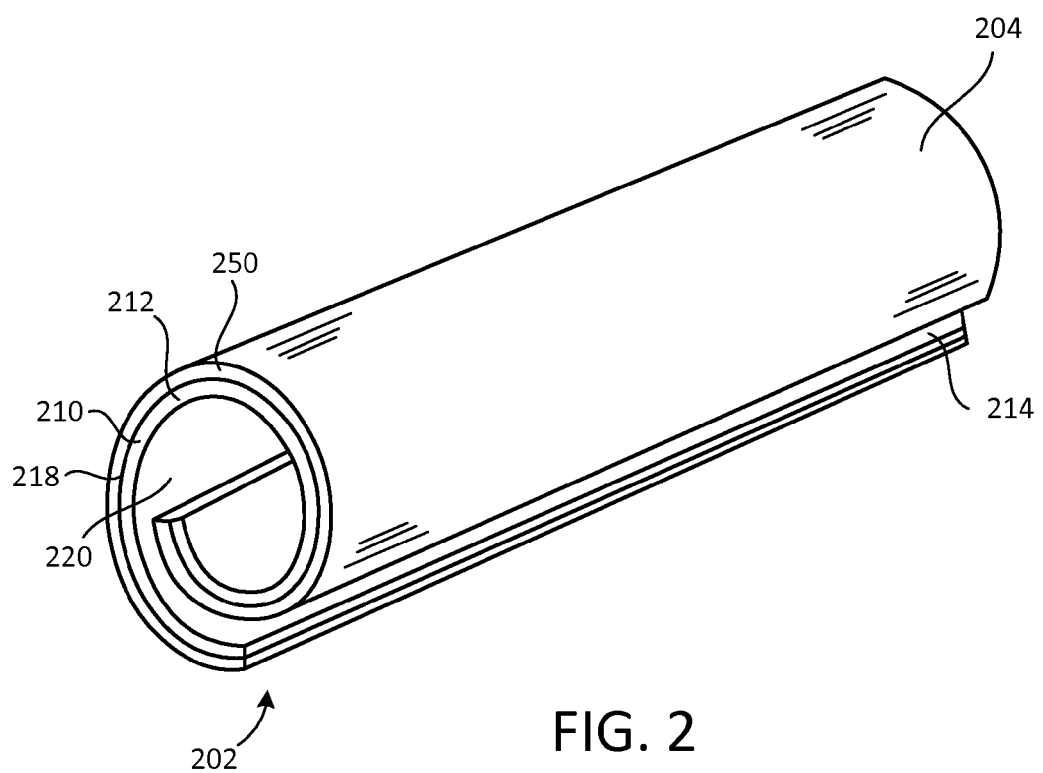
FIG. 2 is a perspective view of a medical device in a collapsed configuration according to an embodiment.
Figure 3:
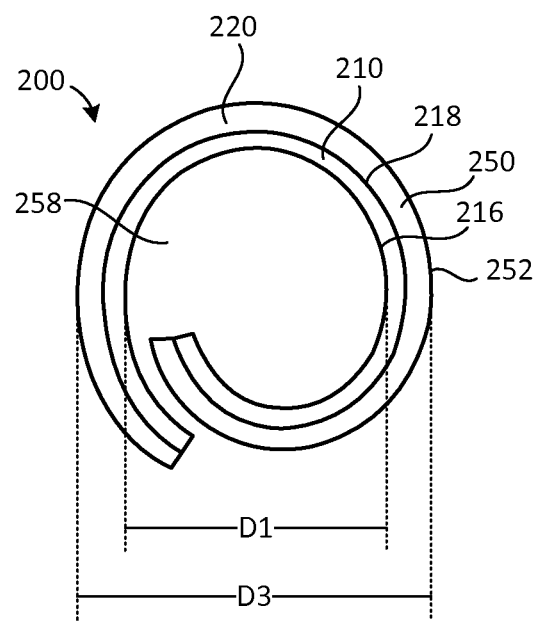
FIG. 3 is an end view of the medical device of FIG. 2 in a collapsed configuration.
Figure 4:
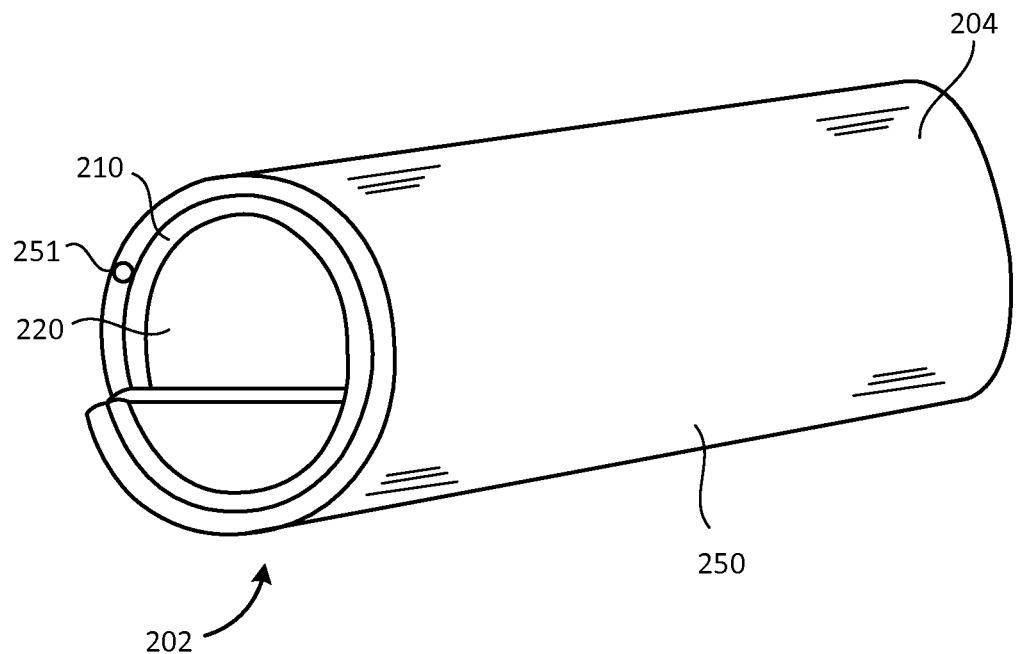
FIG. 4 is a perspective view of the medical device of FIG. 2 in an expanded configuration.
Figure 5:
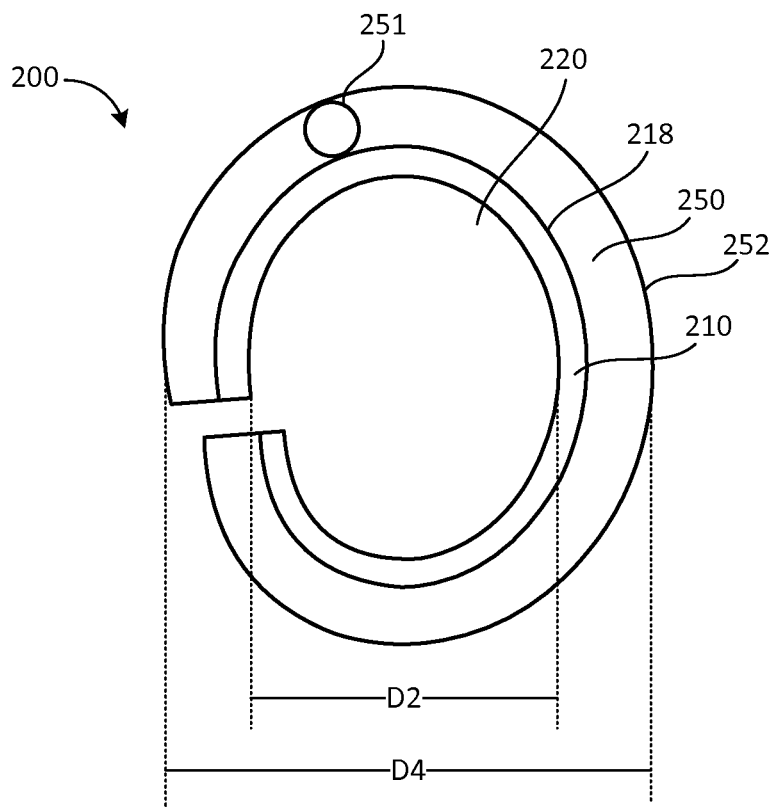
FIG. 5 is an end view of the medical device of FIG. 2 in an expanded configuration.
Figure 5A:
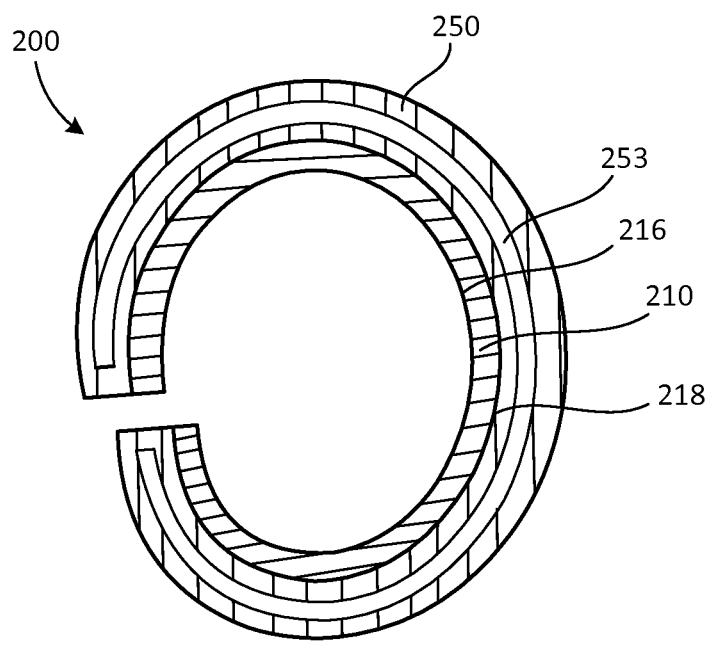
FIG. 5A is a cross-sectional view of the medical device of FIG. 2 in an expanded configuration.

FIGS. 2-6 illustrate a medical device 200 according to an embodiment of the invention. FIG. 2 is a perspective view of the medical device 200 in a collapsed configuration. FIG. 3 is an end view of the medical device 200 in its collapsed configuration. FIG. 4 is a perspective view of the medical device 200 in an expanded configuration. FIG. 5 is an end view of the medical device 200 in its expanded configuration. FIG. 5A is a cross-sectional view of the medical device 200 in its expanded configuration.

The medical device 200 includes an elongate member 210 and an expandable member 250. The expandable member 250 is coupled to an outer surface 218 of the elongate member 210. In some embodiments, the expandable member 250 defines a lumen 258 and the expandable member 250 is coupled to the elongate member 210 such that the elongate member 210 is disposed within the lumen 258 defined by the expandable member 250. In some embodiments, the expandable member 250 surrounds the elongate member 210.

The medical device 200 includes a proximal end portion 202 and a distal end portion 204. The medical device 200 is configured to be inserted into a body of a patient and to dilate bodily tissue to create a lumen through a portion of the body of the patient. The medical device 200 has a collapsed configuration (when the elongate member 210 and the expandable member 250 are in their respective collapsed configurations) and an expanded configuration (when the elongate member 210 and the expandable member 250 are in their respective expanded configuration). As will be discussed in more detail below, the medical device 200 is configured to be placed within the body of the patient when the medical device 200 is in its collapsed configuration. The medical device 200 can then be moved to its expanded configuration. A lumen defined by the medical device may then be used to perform additional medical procedures.

The medical device 200 can be of any length sufficient to extend to the desired locations within the body of the patient. For example, the medical device 200 can be between 28 and 46 cm. In some embodiments, the medical device 200 is shorter than 28 cm. In yet further embodiments, the medical device is longer than 46 cm. In some embodiments, the medical device 200 is of a length sufficient extend from a location outside of a body of a patient to a kidney of the patient.

The elongate member 210 has a proximal end portion 212, a distal end portion 214, an inner surface 216, and an outer surface 218. The elongate member 210 defines a lumen 220. Specifically, the inner surface 216 of the elongate member 210 defines the lumen 220.

The elongate member 210 is configured to be disposed or placed in a first configuration and a second configuration. As best illustrated in FIGS. 2 and 3, the first configuration is a collapsed configuration. As best illustrated in FIGS. 4 and 5, the second configuration is an expanded configuration.

In the illustrated embodiment, the lumen 220 defined by the elongate member 210 has a generally circular cross-section. The lumen 220 defined by the elongate member 210 has a first size when the elongate member 210 is in its collapsed configuration and has a second size when the elongate member 210 is in its expanded configuration. Specifically, as best illustrated in FIG. 3, the lumen 220 defined by the inner surface 216 of the elongate member 210 has a diameter D1 when the elongate member 210 is in its collapsed configuration. As best illustrated in FIG. 5, the lumen 220 defined by the inner surface 216 of the elongate member 210 has a diameter D2 when the elongate member 210 is in its expanded configuration. In the illustrated embodiment, D2 is larger than D1. In some embodiments, diameter D1 is between about 6 F and 9 F (2 mm to 3 mm) and diameter D2 is between about 12 F and 18 F (4 mm and 6 mm). In the illustrated embodiment, the elongate member 210 is biased to its collapsed configuration.

In the illustrated embodiment, the lumen 220 defined by the elongate member 210 is configured to receive another medical device so that such other medical device extends through the lumen 220 defined by the elongate member 210. For example, in some embodiments, when the elongate member 210 is placed within a body of a patient and is in its expanded configuration, another medical device, such as a guidewire or stent, may be inserted into the body of the patient through the lumen 220 defined by the elongate member 210.

In the illustrated embodiment, the elongate member 210 is generally tubular and includes a spiral rolled sheet of material. The spiral rolled sheet of material is formed of a biocompatible plastic material. In other embodiments, the elongate member is made of another biocompatible material. For example, in one embodiment, the elongate member is made of or includes super elastic Nitinol.

The expandable member 250 is configured to be move or convert the elongate member 210 from one configuration to another configuration. For example, in some embodiments, the expandable member 250 is configured to expand the elongate member or move the elongate member from its first, collapsed configuration to its second, expanded configuration.

In the illustrated embodiment, the expandable member 250 is configured to be expanded from a first, collapsed configuration to a second, expanded configuration. As best illustrated in FIG. 3, the expandable member 250 has an outer surface 252 that has a generally circular cross-section. The outer surface 252 of the expandable member 250 is configured to contact bodily tissue of the patient when the medical device 200 is disposed within a body of a patient.

The outer surface 252 has a diameter D3 when the expandable member 250 is in its first, collapsed configuration. As best illustrated in FIG. 5, the outer surface 252 has a diameter D4 when the expandable member 250 is in its expanded configuration. The diameter D4 is larger than the diameter D3.

In the illustrated embodiment, the expandable member 250 is an inflatable member. As best illustrated in FIGS. 4, 5 and 5A, in the illustrated embodiment, the expandable member 250 includes a valve 251. In some embodiments, the valve 251 is operatively coupled to an internal inflation lumen 253. Thus, in such embodiments, the internal inflation lumen 253 of the expandable member 250 may be inflated via the valve 251.

When the inflatable member is moved or expanded from its deflated configuration to its inflated configuration, the elongate member 210 is moved from its collapsed configuration to its expanded configuration. In some embodiments, the expandable member 250 is folded (such as folded upon itself) when it is in its collapsed configuration. In some embodiments, the expandable member 250 is formed of a compliant material and is configured to stretch when it is in its expanded configuration.

Any known means of inflating the inflatable expandable member 250 may be used. For example, in some embodiments, the expandable member 250 includes an inflation lumen and a valve for inflating the expandable member 250. For example, in some embodiments, the expandable member 250 includes a valve and an inflation lumen coupled to a proximal end portion of the expandable member 250.

In other embodiments, the expandable member 150 includes other mechanisms for expanding the elongate member 210 from a first configuration to a second configuration.

The expandable member 250 may be made of any biocompatible material. For example, in some embodiments, the expandable member 250 is made of a biocompatible plastic material.

The expandable member 250 may be coupled to the elongate member 210 using any known method. For example, in some embodiments, an adhesive couples the expandable member 250 to the elongate member 210. In another embodiment, the expandable member 250 is heat welded to the elongate member 210. In yet further embodiments glue or an ultrasonic welding process is used to couple the expandable member 250 to the elongate member 210.

Figure 6:
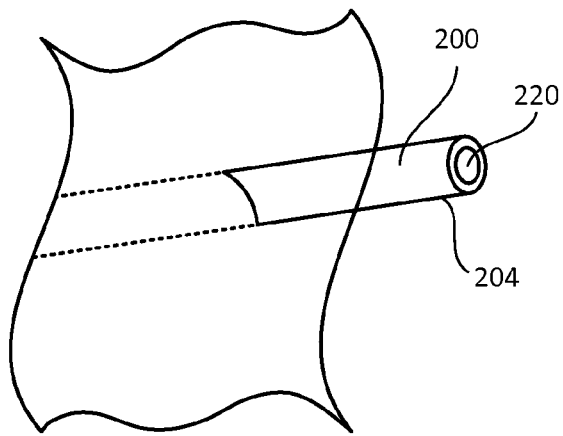
FIG. 6 is a schematic figure of the medical device of FIG. 2 disposed within a body of a patient.

FIG. 6 is a schematic illustration of the medical device 200 partially disposed within a body of a patient. The medical device 200 may be disposed within the body of the patient such that the distal end portion 204 of the medical device 200 is disposed within the body of the patient and the proximal end portion 202 of the medical device 200 extends from the body of the patient.

For example, in one embodiment, medical device 200 may be inserted into the body of the patient such that the distal end portion 204 of the medical device 200 is disposed within a kidney of the patient and the proximal end portion 202 extends from the body of the patient. Thus, the lumen 220 defined by the elongate member 210 fluidically couples the kidney of the patient with the outside of the patient and additional medical procedures may be performed.

Figure 7:
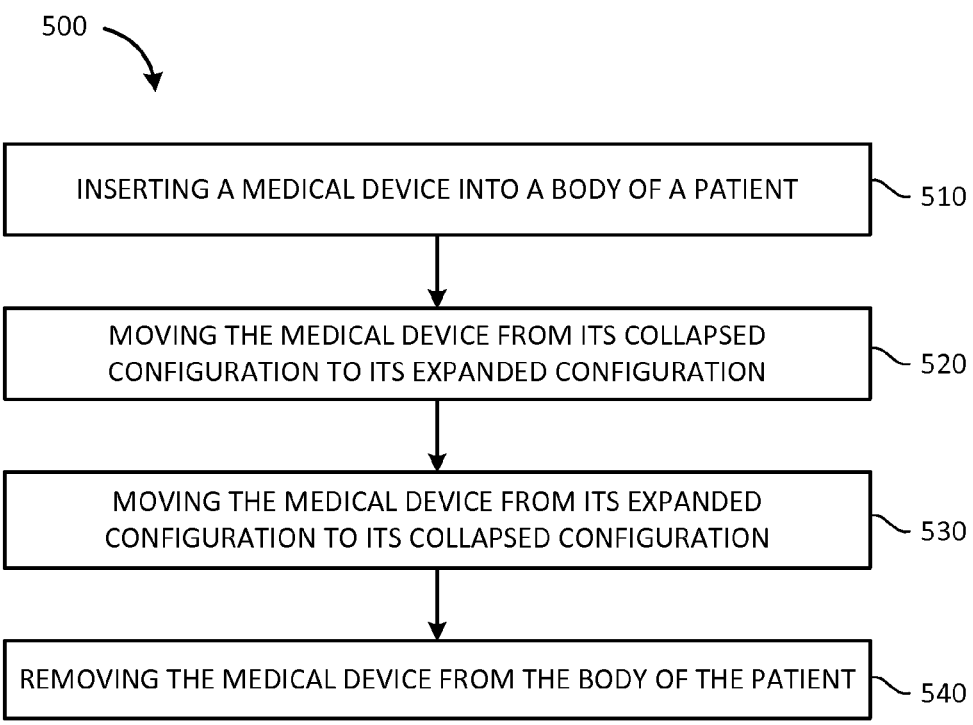
FIG. 7 is a flow chart of a method according to an embodiment.

FIG. 7 is a flow chart for a method 500 according to an embodiment of the invention. The method includes at step 510 inserting the medical device 200 into a body of a patient. At step 520, the medical device 200 is moved from its collapsed configuration to its expanded configuration. At step 530, the medical device 200 is moved from its expanded configuration to its collapsed configuration. At step 540, the medical device 200 is removed from the body of the patient.

In some embodiments, the medical device is moved from its collapsed configuration to its expanded configuration by inflating an expandable member of the medical device. In some embodiments, the removing the medical device from the body of the patient includes removing both the elongate member and the expandable member at the same time.

In some embodiments, the medical device is moved from its expanded configuration to its collapsed configuration by deflating the expandable member.

In some embodiments, the method includes inserting another medical device into the lumen defined by the elongate member after moving the medical device from its collapsed configuration to is expanded configuration. In some embodiments, the method includes inserting another medical device into the lumen defined by the elongate member after moving the medical device from its collapsed configuration to its expanded configuration and before removing the medical device from the body of the patient. In such embodiments, the another medical device is disposed within the lumen defined by the elongate member before the expandable member is removed from the body of the patient.

In some embodiments, the medical device is inserted into a body of a patient such that the distal end portion of the medical device is within the body of the patient and the proximal end portion of the medical device extends from the body of the patient. In some embodiments, the medical device is inserted such that the distal end portion is disposed within a kidney of the patient.

In one embodiment, a medical device includes an elongate member and an expandable member. The elongate member has an inner surface and an outer surface. The inner surface defines a lumen. The elongate member has a collapsed configuration and an expanded configuration. The elongate member is biased to its collapsed configuration. The expandable member is coupled to the outer surface of the elongate member. The expandable member is configured to move the elongate member from its collapsed configuration to its expanded configuration.

In one embodiment, the expandable member is an inflatable member. In another embodiment, the expandable member has a first configuration and a second configuration. The expandable member is configured to move the elongate member from its collapsed configuration to its expanded configuration in response to the expandable member moving from its first configuration to its second configuration.

In one embodiment, the expandable member has a first configuration and a second configuration. The expandable member is configured to move the elongate member from its collapsed configuration to its expanded configuration in response to the expandable member moving from its first configuration to its second configuration. The expandable member has a first size when the expandable member is in its first configuration. The expandable member has a second size when the expandable member is in its second configuration. The second size is larger than the first size.

In some embodiments, the lumen defined by the inner surface of the elongate member has a first size when the elongate member is in its collapsed configuration. The lumen defined by the inner surface of the elongate member has a second size when the elongate member is in its expanded configuration. The second size is larger than the first size.

In some embodiments, the lumen defined by the inner surface of the elongate member has a first diameter when the elongate member is in its collapsed configuration. The lumen defined by the inner surface of the elongate member has a second diameter when the elongate member is in its expanded configuration. The second diameter is larger than the first diameter.

In some embodiments, the elongate member includes a rolled sheet of material. In some embodiments, the expandable member surrounds the elongate member. In some embodiments, the expandable member defines a lumen. The elongate member is disposed within the lumen defined by the expandable member.

In one embodiment, a medical device includes an elongate member and an expandable member. The elongate member defines a lumen. The elongate member has an expanded configuration and a collapsed configuration. The elongate member is biased to its collapsed configuration. The expandable member is disposed outside of the lumen defined by the elongate member. The expandable member is configured to move the elongate member from its collapsed configuration to its expanded configuration.

In some embodiments, the expandable member is an inflatable member. In some embodiments, the expandable member defines a lumen and the elongate member is disposed within the lumen defined by the expandable member. In some embodiments, the lumen defined by the elongate member has a first size when the elongate member is in its collapsed configuration and a second size when the elongate member is in its expanded configuration. The second size is greater than the first size.

In some embodiments, a method includes (a) inserting a medical device into a body of a patient, the medical device having an elongate member and an expandable member, the medical device having a collapsed configuration and an expanded configuration, (b) moving the medical device from its collapsed configuration to its expanded configuration while the medical device is disposed within the body of the patient, (c) moving the medical device from its expanded configuration to its collapsed configuration while the medical device is disposed within the body of the patient, and (d) removing the medical device from the body of the patient.

In some embodiments, the expandable member is an inflatable member and the moving the medical device from its collapsed configuration to its expanded configuration includes inflating the expandable member.

In some embodiments, the method includes inserting another medical device within a lumen defined by the elongate member after the moving the medical device from its collapsed configuration to its expanded configuration.

In some embodiments, the expandable member is an inflatable member and defines a lumen, the elongate member is disposed within the lumen defined by the inflatable member, and the moving the medical device from its collapsed configuration to its expanded configuration includes inflating the expandable member.

In some embodiments, the removing includes removing the elongate member and the expandable member.

In some embodiments, the removing includes removing the elongate member from the body of the patient while removing the expandable member from the body of the patient.

In some embodiments, the elongate member defines a lumen and the expandable member is coupled to the elongate member and is disposed outside of the lumen defined by the elongate member.

While certain features of the described implementations have been illustrated as described herein, many modifications, substitutions, changes and equivalents will now occur to those skilled in the art. It is, therefore, to be understood that the appended claims are intended to cover all such modifications and changes as fall within the scope of the embodiments.

What is claimed is:

1. A medical device, comprising:
 a tubular member having first and second edges extending an entire length of the medical device from a distal end to a proximal end, the second edge being spaced apart from the first edge in either the collapsed or expanded configuration, the tubular member including:
 an elongate member having an inner surface and an outer surface, the elongate member defining a lumen, the lumen including a space within the inner surface of the elongate member, at least a portion of the inner surface of the elongate member being directly exposed to the space of the lumen, the elongate member having a collapsed configuration and an expanded configuration, the elongate member being biased to the collapsed configuration; and
 an expandable member having an inner surface, the inner surface of the expandable member being coupled to the outer surface of the elongate member, the expandable member being configured to move the elongate member from the collapsed configuration to the expanded configuration,
 wherein the expandable member is an inflatable member.

2. The medical device of claim 1, wherein the expandable member has a first configuration and a second configuration, the expandable member being configured to move the elongate member from the collapsed configuration to the expanded configuration in response to the expandable member moving from the first configuration to the second configuration.

3. The medical device of claim 1, wherein the expandable member has a first configuration and a second configuration, the expandable member being configured to move the elongate member from the collapsed configuration to the expanded configuration in response to the expandable member moving from the first configuration to the second configuration, the expandable member having a first size when the expandable member is in the first configuration, the expandable member having a second size when the expandable member is in the second configuration, the second size being larger than the first size.

4. The medical device of claim 1, wherein the lumen defined by the elongate member has a first size when the elongate member is in the collapsed configuration, the lumen defined by the elongate member has a second size when the elongate member is in the expanded configuration, the second size being larger than the first size.

5. The medical device of claim 1, wherein the lumen defined by the elongate member has a first diameter when the elongate member is in the collapsed configuration, the lumen defined by the elongate member has a second diameter when the elongate member is in the expanded configuration, the second diameter being larger than the first diameter.

6. The medical device of claim 1, wherein the elongate member includes a rolled sheet of material.

7. The medical device of claim 1, wherein the inner surface of the expandable member surrounds all portions of the outer surface of the elongate member, the expandable member including an internal inflation lumen, the internal inflation being a single elongated pocket.

8. The medical device of claim 1, wherein the expandable member defines a lumen between the inner surface and an outer surface of the expandable member.

9. A medical device, comprising:
a tubular member having first and second edges extending an entire length of the medical device from a distal end to a proximal end, the second edge being spaced apart from the first edge in either the collapsed or expanded configuration, the tubular member including:
an elongate member including an inner surface and an outer surface, the elongate member defining a lumen, the lumen including a space within the inner surface of the elongate member, at least a portion of the inner surface of the elongate member being directly exposed to the space of the lumen, the elongate member having an expanded configuration and a collapsed configuration, the elongate member being biased to the collapsed configuration; and
an expandable member disposed outside of the lumen defined by the elongate member, the expandable member including an inner surface and an outer surface opposite to the inner surface, the inner surface of the expandable member being coupled to the outer surface of the elongate member, the expandable member configured to move the elongate member from the collapsed configuration to the expanded configuration,
wherein the expandable member defines a lumen between the inner surface and the outer surface of the expandable member;
wherein the expandable member is an inflatable member.

10. The medical device of claim 9, wherein the lumen defined by the inner surface of the elongate member has a first size when the elongate member is in the collapsed configuration and a second size when the elongate member is in the expanded configuration, the second size being greater than the first size.

11. A method, comprising:
inserting a medical device into a body of a patient, the medical device having an elongate member and an expandable member, the elongate member having an inner surface and an outer surface, the elongate member defining a lumen, the lumen including a space within the inner surface of the elongate member, at least a portion of the inner surface of the elongate member being directly exposed to the space of the lumen, the medical device having a collapsed configuration and an expanded configuration, the expandable member including an inner surface and an outer surface opposite to the inner surface, the inner surface of the expandable member being coupled to the outer surface of the elongate member such that the inner surface of the expandable member overlaps with the outer surface of the elongate member;
moving the medical device from the collapsed configuration to the expanded configuration while the medical device is disposed within the body of the patient;
moving the medical device from the expanded configuration to the collapsed configuration while the medical device is disposed within the body of the patient; and
removing the medical device from the body of the patient;
wherein the medical device defines a tubular member having first and second edges extending an entire length of the medical device from a distal end to a proximal end, the second edge being spaced apart from the first edge in either the collapsed or expanded configuration.

12. The method of claim 11, wherein the expandable member is an inflatable member and the moving the medical device from the collapsed configuration to the expanded configuration includes inflating the expandable member.

13. The method of claim 11, further comprising:
inserting another medical device within the lumen defined by the elongate member after the moving the medical device from the collapsed configuration to the expanded configuration.

14. The method of claim 11, wherein the expandable member is an inflatable member and defines a lumen, and the moving the medical device from the collapsed configuration to the expanded configuration includes inflating the expandable member.

15. The method of claim 14, wherein the removing includes removing the elongate member and the expandable member.

16. The method of claim 11, wherein the removing includes removing the elongate member from the body of the patient while removing the expandable member from the body of the patient.

* * * * *